(12) United States Patent
Dykes

(10) Patent No.: US 6,884,240 B1
(45) Date of Patent: Apr. 26, 2005

(54) PROTECTION SYSTEM FOR SURGICAL INSTRUMENTS

(76) Inventor: Ronald Dykes, 2203 Timberloch Pl., Suite 130, The Woodlands, TX (US) 77380

( * ) Notice: Subject to any disclaimer, the term of this patent is extended or adjusted under 35 U.S.C. 154(b) by 404 days.

(21) Appl. No.: 10/016,984

(22) Filed: Dec. 7, 2001

(51) Int. Cl.$^7$ ............................................. A61B 17/32
(52) U.S. Cl. ........................... 606/1; 606/167; 30/162; 30/286
(58) Field of Search ............................... 606/167, 166, 606/172, 1; 30/162, 286

(56) References Cited

U.S. PATENT DOCUMENTS

| | | |
|---|---|---|
| 3,706,106 A | 12/1972 | Leopoldi |
| 3,905,101 A | 9/1975 | Shepherd |
| 3,945,117 A | 3/1976 | Beaver |
| 4,342,208 A | 8/1982 | Evans |
| 4,414,974 A | 11/1983 | Dotson et al. |
| 4,496,163 A | 1/1985 | Bernfeld |
| 4,499,898 A | 2/1985 | Knepshield et al. |
| 4,527,406 A | 7/1985 | Baker |
| 4,552,146 A * | 11/1985 | Jensen et al. ............... 606/166 |
| 4,569,133 A * | 2/1986 | Schmidt ..................... 606/172 |
| 4,576,164 A | 3/1986 | Richeson |
| 4,688,570 A | 8/1987 | Kramer et al. |
| 4,735,202 A | 4/1988 | Williams |
| 4,759,363 A * | 7/1988 | Jensen ........................ 606/172 |
| 4,768,509 A | 9/1988 | Grosvenor et al. |
| 5,254,128 A | 10/1993 | Mesa |
| 5,275,606 A * | 1/1994 | Abidin et al. ............... 606/167 |
| 5,417,704 A * | 5/1995 | Wonderley ................. 606/167 |
| 5,545,172 A | 8/1996 | Knepshield et al. |
| 5,578,050 A | 11/1996 | Webb |
| 5,657,541 A | 8/1997 | Hickok et al. |
| 5,830,226 A * | 11/1998 | Webb et al. ................ 606/167 |
| 5,868,771 A * | 2/1999 | Herbert et al. ............. 606/167 |
| 5,873,148 A | 2/1999 | Arnold |
| 5,908,432 A | 6/1999 | Pan |
| 5,951,579 A | 9/1999 | Dykes |
| 6,022,364 A | 2/2000 | Flumene et al. |
| 6,053,929 A | 4/2000 | Cohn et al. |
| 6,113,606 A | 9/2000 | Dykes |
| 6,122,828 A | 9/2000 | Asterino, Jr. |
| 6,129,740 A | 10/2000 | Michelson |
| 6,197,006 B1 | 3/2001 | Wiklund |
| 6,202,862 B1 | 3/2001 | Acquaviva et al. |

\* cited by examiner

*Primary Examiner*—Michael H. Thaler

(57) ABSTRACT

A protection system for surgical instruments having a body with an instrument at one end. A movable guard is provided that moves between locked open and locked closed positions. The guard includes a grip and an opening to provide access for cleaning.

8 Claims, 3 Drawing Sheets

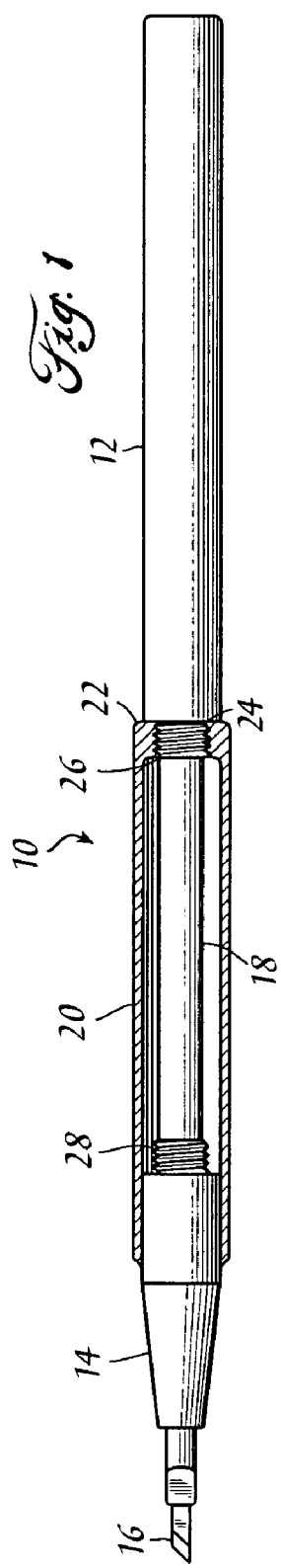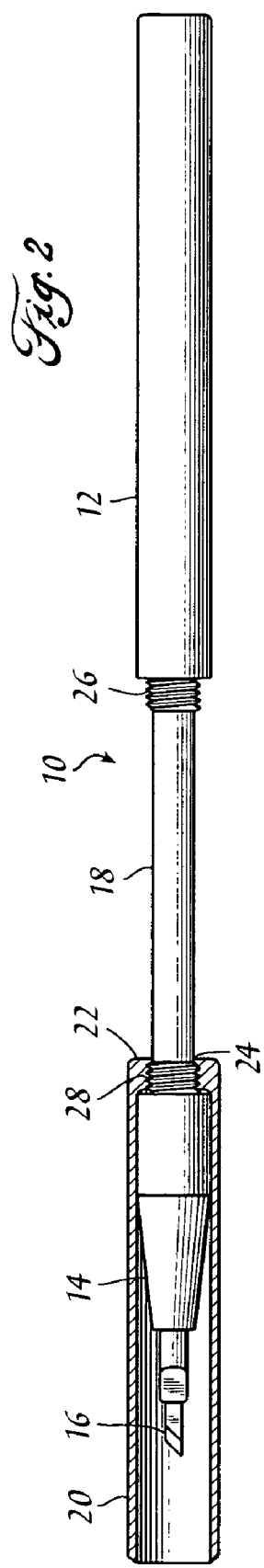

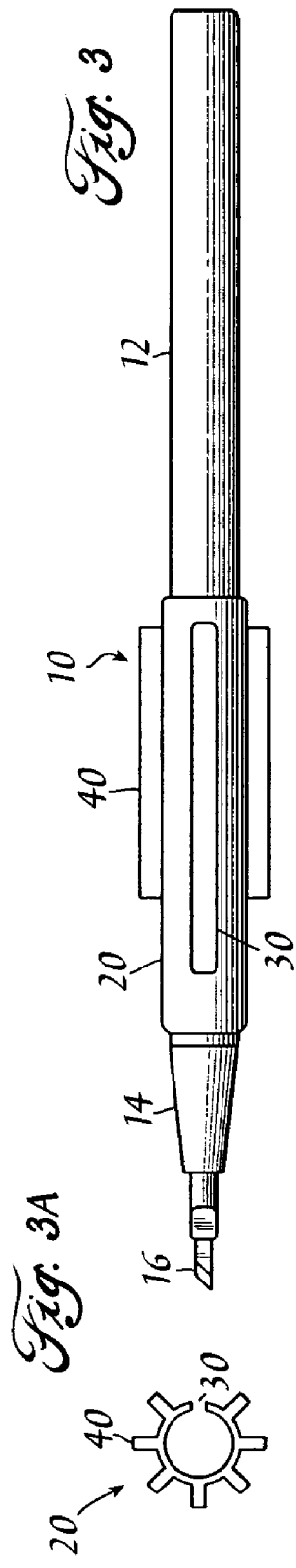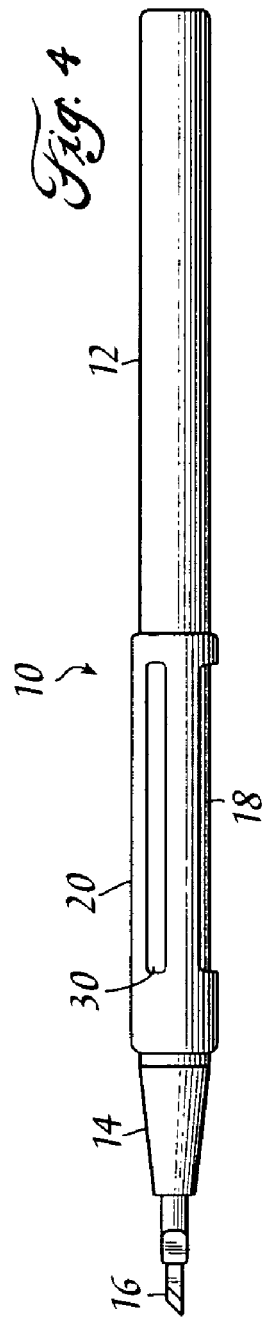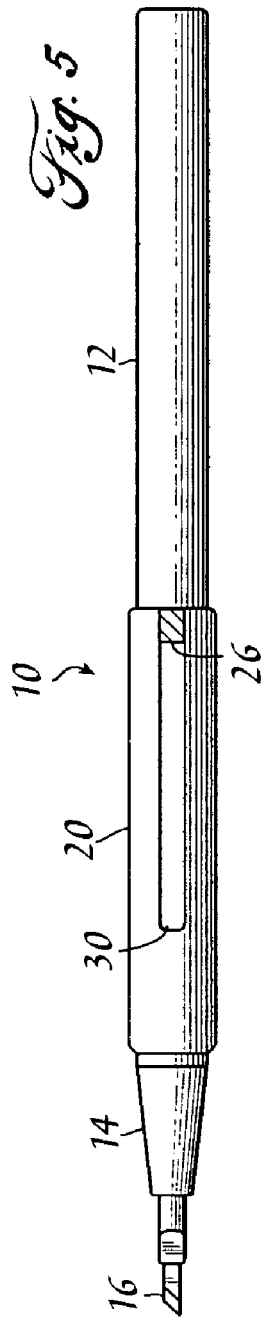

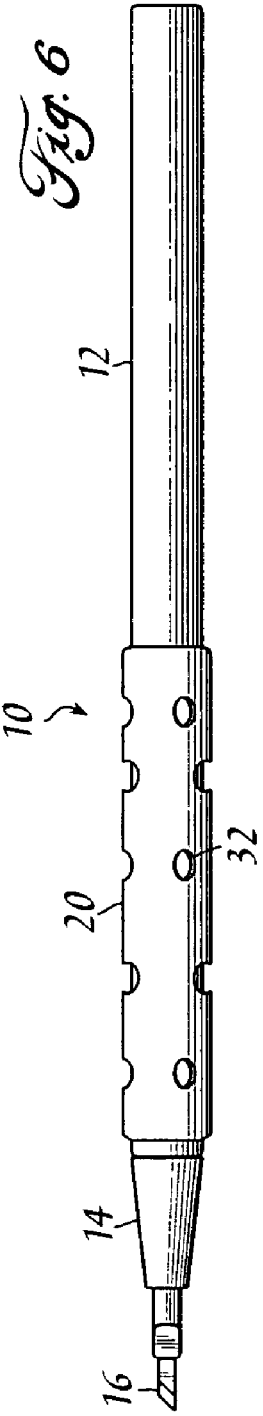
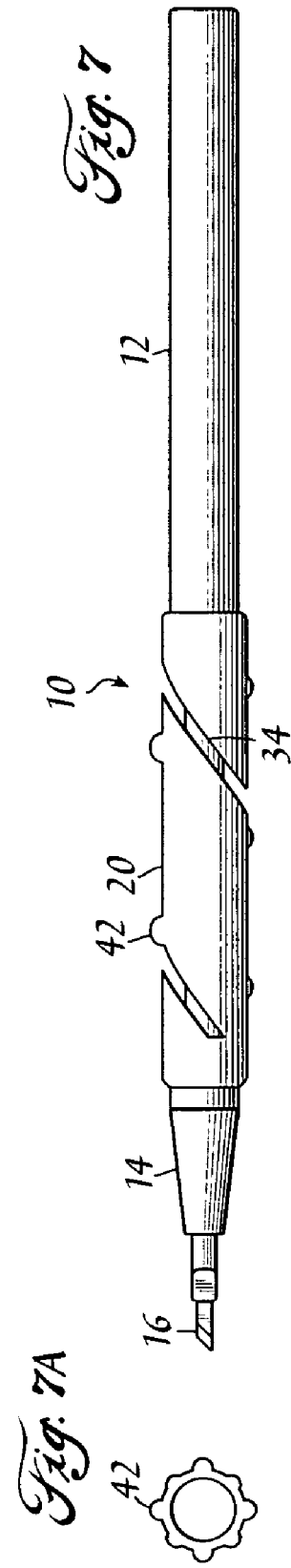
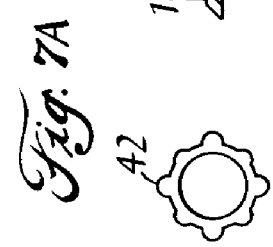

PROTECTION SYSTEM FOR SURGICAL INSTRUMENTS

BACKGROUND OF THE INVENTION

This invention relates to surgical instruments, and more particularly to protection of delicate instrument parts or the sharp points or blades located at a distal end of such surgical instruments, wherein the protection system prevents injury to a person or damage to the instrument.

Surgical instruments may include a sharp point or cutting blade. Others are extremely delicate. Examples of such instruments include hooks (such as Sinskey hooks, Bonn hooks, insertion hooks, twist hooks and the like), scissors (such as retinal scissors and the like), picks (such as retinal picks and the like), forceps, probes, lens manipulators, markers, collar buttons, choppers, cystotomes irrigation needles and cannulas, spatulas (such as Castroviejo spatulas and the like), and dilators. Most often, these instruments include at least one generally cylindrical handle with a distal end that houses a delicate member, sharp point, or cutting blade. Surgical knives that include a cutting blade at a distal end of the handle are typical of such instruments, and much of the prior art pertaining to protection for such instruments is directed at protection for surgical knives. However, the instant invention applies equally to the protection of non-sharp instruments.

Surgical instruments typically have a body with a cutting blade or other operable instrument at one end of the body. The end of the body with the instrument sometimes has a portion that tapers down towards the instrument to provide good visibility of the instrument tip. The instruments can be extremely sharp, and the extreme sharpness may render them hazardous when passed back and forth during use in surgical operations. If the instrument has already been used on the patient, then there is a potential danger of infection since any sharp or tapered instrument can very easily cut or rip through a surgical glove and the skin beneath the glove.

In general, prior art systems for protection of surgical knives include some form of mechanically operable shield that covers the cutting blade when not in use, and that may be moved or removed in order to expose the cutting blade during use. A discussion of the prior art pertaining to protection for surgical knives is generally applicable to the different types of surgical instruments mentioned above.

U.S. Pat. No. 4,576,164 to Richeson discloses a disposable micro-surgical knife having a shroud that can be locked into a position protecting the blade. The shroud is in the form of a cylindrical sheath that moves axially along and around the knife body. In addition, the shroud has a plurality of projections which mate with a series of longitudinal and circumferential grooves formed in the exterior of the knife body. This arrangement of grooves on the knife body and projections on the shroud allow the shroud to be locked in two or three different axial positions on the knife body. In one position the shroud acts as an enlarged handle, and in a different position the shroud acts as a protective device for the blade and blade edges. However, if the shroud is damaged or slips off and is lost, then the knife body has undesirable grooves on its outer surface that may be uncomfortable to a surgeon using the knife.

U.S. Pat. No. 4,414,974 to Dodson, et al. discloses a surgical knife with a shroud similar to the one disclosed by Richeson. However, the surgical knife of Dodson et al. does not have a shroud with projections, and it does not have longitudinal or circumferential grooves on the exterior surface of the knife body. Instead, the surgical knife of Dodson et al. relies upon friction between oversized portions of the body and the opening in the shroud for a friction fit. In one axial position the shroud is retracted for use and in another axial position the shroud is in a blade protective position. However, if the friction fit is inadequate, the shroud may slip from its desired position thereby resulting in safety hazards and potential damage to the knife blade.

U.S. Pat. No. 4,735,202 to Williams discloses a disposable micro-surgical knife having a blade guard. The blade guard is basically a cylindrical sleeve that has a longitudinal slot that extends to one end of the sleeve. The knife body has a small locking tab adjacent the forward tapered portion of the knife. The blade guard slides onto the knife body from the rear until the locking tab enters the longitudinal slot and the guard is rotated to be locked into place. Thus, the blade guard can be locked into a blade covering position and then totally removed from the knife body for use of the knife. However, this blade guard may be easily damaged or lost after removal, thereby defeating its purpose.

Similarly, U.S. Pat. No. 4,768,509 to Grosvenor et al. discloses a removable external blade guard. U.S. Pat. Nos. 3,706,106; 3,905,101; and 3,945,117 disclose other types of surgical knives having movable or removable blade protective structures. These knives suffer from the same or similar limitations as described above.

U.S. Pat. No. 5,254,128 to Mesa (incorporated herein by reference) discloses a surgical knife with a blade protector axially moveable between two positions, namely, opened for normal use and closed for storage or safe handling. The blade protector may be fixed in either position by two sets of threads, one set on the knife handle and another matching set at both ends of the blade protector. While this arrangement solves some of the limitations of the prior art described above, other common limitations still exist. For example, with the surgical knife of Mesa, debris is often trapped under the blade protector and between the opposing sets of male and female threads, thereby preventing or inhibiting thorough cleaning or sterilizing. In addition, safety concerns may arise due to the nearly uniform appearance of both ends of the surgical instrument body, thereby making it difficult to see which end of the body houses the instrument and what particular type of instrument is attached to the body, especially with small instruments which may be less than 3 millimeters in diameter. Moreover, the smooth outer surface of the blade protector makes it difficult to open or close the blade protector with one hand (as the factor considered by OSHA regulations pertaining to medical "sharps"), and often causes the surgical instrument to roll off the sterile field and potentially damage the instrument.

These and other limitations and disadvantages of the prior art are overcome by the present invention, which provides an improved protection system for surgical instruments, wherein the instrument is provided with a movable protector for preventing injury to handlers and damage to the instrument when not in use.

SUMMARY OF THE INVENTION

In a preferred embodiment of the present invention, the surgical instrument is equipped with a movable protector or guard. The surgical instrument may be a scalpel or any number of other delicate or sharp instruments, such as hooks, scissors, forceps, probes, manipulators, markers, choppers, collar buttons, cystotomes, needles, cannulas, spatulas or dilators. The guard is a generally cylindrical sleeve that may be moved axially along the body to one of two locked positions. In a first position, the guard is locked forward (or closed) to substantially surround and protect the instrument. In a second position, the guard is locked aft in a retracted position (or open) to expose the instrument for normal use.

In order to facilitate movement of the guard to and from the locked open or locked closed positions using as single hand (as the criteria suggested by OSHA regulations), the guard may be provided with a grip disposed about its exterior surface. The grip may be a series of external ridges, nubs, bumps, or undulations formed to match a user's grip, or any number of other forms of protrusions. The grip preferably also creates a non-cylindrical exterior of the guard in order to prevent the surgical knife from inadvertently rolling off a sterile surgical field.

Reusable surgical instruments must be cleaned and sterilized between uses. The present invention preferably includes a guard with one or more openings or gaps therethrough in order to expose a portion of the underlying body of the instrument. These openings or gaps facilitate the entry of cleaning agents and sterilizing steam into the small, otherwise covered spaces under the guard, without the need to remove (and potentially lose) the guard.

Whereas prior art protection systems may require moving or removing the means for protecting the instrument in order to identify its type and/or size, the present invention may include a translucent guard that does not need to be removed in order to accomplish these objectives. A translucent guard also enhances safety of the protection system by enabling a user to quickly and easily distinguish between the handle portion of the body and the distal end housing the potentially dangerous and delicate instrument.

The exterior of the body and the interior of the guard may include threads to allow the guard to be moved axially, rotated, and threadedly locked open or locked closed. A first set of threads may be included on the exterior of an intermediate, reduced diameter portion of the body as a means for slidably moving the guard along and around the body. Preferably, two sets of external threads are spaced apart axially on the exterior of an intermediate, reduced diameter portion of the body. Matching threads are employed on the interior of the guard. In this manner, the two sets of threads provide a means for locking the guard in the open or closed position, i.e., by threaded engagement between the internal threads of the guard and one of the two sets of threads on the body. Similarly, the axial spacing between the two sets of threads on the body of the body provides for free axial movement of the guard when the threads are disengaged. Accordingly, the guard can be positively locked in the open or closed position. When the guard is locked closed surrounding the instrument, persons handling the blade are not exposed to potential injuries and the instrument is protected from damage due to improper handling. On the other hand, when the guard is locked open, it acts as an integral and secure portion of the body and does not interfere with (and may enhance) the natural operation of the surgical instrument.

Other means may be used to provide axial movement of the guard and lock it in an open or closed position. For example, grooves and matching lugs (either friction or spring-loaded) may be formed on the exterior of the body and the interior of the guard. Alternatively, spiral channels and matching detents (either friction or spring-loaded) may be formed on the exterior of the body and the interior of the guard. Further alternatives may include spring loaded balls fitted with grooves, or other spring-type devices. While the threads mentioned above are preferable, any of the previous locking means, or combinations thereof, may be suitable so long as they provide for axial movement and locking of the guard in an open or a closed position.

If threads are used, the openings or gaps of the instant invention may be extended through the threads. While such a feature permits cleaning and sterilization of the threads, it also permits the threads to "skip" if the guard is overtightened. In this way, torque on the guard is limited so that the instrument remains easily accessible at all times.

The foregoing has outlined the features and technical advantages of the present invention in order that the detailed description of the invention that follows may be better understood. Additional features and advantages of the invention will be described hereinafter which form the subject of the claims of the invention.

DRAWINGS

For a more complete understanding of the present invention, and the advantages thereof, reference is now made to the following description, taken in conjunction with the accompanying drawings, in which FIG. 1 is a side view of a surgical knife with a cross-sectional view of the attached, movable guard of the present invention positioned in a locked open position.

FIG. 2 is a side view of a surgical knife with a cross-sectional view of the attached, movable guard of the present invention positioned in a locked closed position.

FIG. 3 is a side view of a surgical knife with an alternative embodiment of the attached, movable guard of the present invention positioned in a locked open position.

FIG. 3A is a corresponding end view of the guard shown in FIG. 3.

FIG. 4 is a side view of a surgical knife with another alternative embodiment of the attached, movable guard of the present invention positioned in a locked open position.

FIG. 5 is a side view of a surgical knife with yet another alternative embodiment of the attached, movable guard of the present invention positioned in a locked open position.

FIG. 6 is a side view of a surgical knife with yet another alternative embodiment of the attached, movable guard of the present invention positioned in a locked open position.

FIG. 7 is a side view of a surgical knife with yet another alternative embodiment of the attached, movable guard of the present invention positioned in a locked open position.

FIG. 7A is a corresponding end view of the guard shown in FIG. 7.

DETAILED DESCRIPTION

Refer now to the drawings, wherein the depicted elements are not necessarily shown to scale and wherein like or similar elements are designated by the same reference numeral through the several views.

Referring now to FIG. 1, a preferred embodiment of the present invention is shown incorporated on a surgical instrument. FIG. 1 is a partial cross-sectional view of the attached, movable protector or guard 20. Again, as mentioned above, many reusable surgical instruments include at least one generally cylindrical handle with a distal end that houses a sharp or delicate instrument. Surgical knives, as more fully described below in accordance with preferred embodiments of the present invention, are typical of such reusable surgical instruments. Although a surgical knife is illustrated in this specification, those skilled in the art will readily appreciate that the instant invention applies equally to all sharp or delicate instruments, all falling within this invention.

In FIG. 1, the surgical knife includes a body 10 with a generally cylindrical handle portion 12 aft and a tip portion 14 forward. The tip 14 may have a flat distal end or, as is often the cases a frustoconical distal end. As would be understood by those skilled in the art, tip 14 also includes an appropriate means (not shown) for mounting the cutting blade 16. The blade 16 may be a diamond or other gem, metal or synthetic blade that will, with proper handling, keep a very sharp edge over repeated uses. In alternative embodiments, the blade 16 may be replaced by any surgical instrument. In other embodiments, the blade 16 or other instrument may be disposable or single-use.

FIG. 1 also shows a reduced diameter portion 18 of the knife body 10 disposed between and interconnected with the handle portion 12 and the tip 14. Guard 20 (shown in a locked open position) has an end wall portion 22 forming an opening disposed around the reduced diameter portion 18. In this embodiment, end wall portion 22 includes interior female threads 24 which engage with male threads 26 formed on the exterior of reduced diameter portion 18. Thus, guard 20 may be rotated to engage its threads 24 with the threads 26 in order to lock the guard 20 in an open position so that the surgical knife may be used normally. In this locked open position, guard 20 generally covers reduced diameter portion 18 in order to form a natural extension of the handle portion 12.

Guard 20 is preferably formed from a translucent material through which a person handling the surgical knife in the safe or locked open position may be able to view the attached blade 16 without the necessity of moving the guard 20 to the unsafe or locked open position. This configuration reduces the potential for selecting an improper surgical knife during surgery by permitting rapid visual identification of the particular size and type of blade 16. This configuration also improves safety during routine handling of the surgical knife by visibly differentiating the handle portion 12 from the distal end of the surgical knife containing blade 16.

As would be understood by those skilled in the art, body 10 and guard 20 should in the preferred, reusable embodiment be formed from hard, durable, and heat resistant plastics, composites, fiber-impregnated resins, or metals. When it is desirable to employ a translucent guard 20 as above, it should be formed from suitable translucent plastics. These types of materials are resistant to the heat and fluids required to clean and sterilize surgical instrument after each use.

FIG. 2 shows the present invention with the guard 20 locked closed to protect the blade 16. Here, guard 20 has been moved forward in the direction of tip 14 of the body 10. From the locked-open position discussed above, the locked-closed position is achieved by counter-rotating guard 20 to disengage threads 24 and 26 so that a user may slide guard 20 forward and engage threads 24 with a second set of threads, threads 28, formed on the exterior of reduced diameter portion 18 forward of threads 24.

Guard 20 is a generally a cylindrical sleeve having an inside diameter that is slightly greater than the corresponding outside diameter of the generally cylindrical portion of the forward tip 14. When reduced diameter portion 18 is employed, the inside diameter of the opening formed by the end wall portion 22 should be slightly greater than the outside diameter of reduced diameter portion 18.

FIGS. 1 and 2 depict the outside diameter of the generally cylindrical portion of the forward tip 14 as having generally the same outside diameter as that of the handle portion 12 of the knife body 10. However, it should be readily apparent that the outside diameter of the forward tip 14 need not be the same as the outside diameter of handle portion 12. However, in order to function properly so as to lock guard 20 in a closed position, the outside diameter the tip 14 should be less than the inside diameter of the guard 20. Preferably, when reduced diameter portion 18 is employed, the handle portion 12 of the body 10 should include at least a portion of larger diameter than the outside diameter of the reduced diameter portion 18. This preferred arrangement facilitates securely locking guard 20 in an open position by forming a screw stop to mechanically prevent end wall portion 22 of guard 20 from extending onto handle portion 12 and past threads 24. Similarly, the outside diameter of the generally cylindrical portion of forward tip 14 must be larger than the outside diameter of the reduced diameter portion 18 to serve as a forward physical stop when the guard 20 is in the locked closed or instrument protective position. Moreover, handle portion 12 need not have the same diameter along its entire length; for some embodiments, handle portion 12 might have a tapered configuration (not shown), with the narrow portion of the taper at the end of the knife 10 opposite the blade 16.

In general, the distance between the threads 26 and 28 on portion 18 should be sufficient to allow for the length of guard 20 to cover threads 28 when the guard is in the locked open position, and allow guard 20 to extend somewhat beyond blade 16 when the guard 20 is placed in the locked closed position. Similarly, the length of guard 20 is selected so that it will extend beyond blade 16 when in the locked closed position, and is thus dependent upon the length of tip 14 and any mounting for blade 16, as well as the length of blade 16 when mounted. Once the approximate position of threads 28 (or other locking means) are selected, then the length of guard 20 may be determined; then the position of threads 24 (or other locking means) determined; and finally the length of reduced diameter portion 18 may be determined.

Reusable surgical instruments must be cleaned and sterilized between uses. As is understood by those skilled in the art, this process typically involves exposing the surgical knife to cleaning agents and high temperature sterilization (such as steam autoclaves, etc.). The present invention includes a guard with one or more slots, openings, or gaps therethrough sufficient to expose portions of the underlying body to the cleaning mechanisms and sterilizing steam. FIGS. 3 and 3A illustrate guard 20 with a slot 30 formed through a wall of the generally cylindrical, sleeve-shaped guard 20. As would be understood by those skilled in the art with reference to this specification, slot 30 facilitates the entry of cleaning agents and sterilizing steam into the small, otherwise covered spaces under the guard 20, without the need to remove and potentially lose the guard 20. As is illustrated in FIGS. 4 through 7A, alternative openings may be formed in guard 20 to serve this same purpose.

For example, FIG. 4 shows multiple slots 30 (designated with the single reference numeral 30) formed at different points around the circumference of guard 20 in order to facilitate the flow of cleaning agents and sterilizing steam from several different angles around the circumference of guard 20. Similarly, FIG. 5 shows a single slot 30 as shown in FIG. 3, but extending through threads 24 of guard 20. The configuration shown in FIG. 5 facilitates direct exposure of threads 24 and threads 26 to cleaning and sterilizing agents. A multitude of alternative openings may be provided in different shapes, sizes, and positions in order to facilitate cleaning and sterilizing. Examples are shown in FIG. 6, which illustrates a plurality of holes 32 (shown with common reference) in guard 20, and FIG. 7, which illustrates a spiral opening 34, both of which facilitate cleaning and sterilizing the underside of guard 20, portion 18, and threads 24 and 28 (or other locking means).

In an alternative to the embodiment as shown in FIG. 5 where the single slot 30 extends through threads 24 of guard 20, the slot 30 may be extended beyond the threads 24. Such a configuration permits the threads 24 on the guard 20 to expand if the guard 20 is overtightened on the body 12. Expansion of the threads 24 on the guard 20 permits those threads 24 to "skip" on the threads 26 on the body 12. As a result, the guard 20 is protected against overtightening, because excess torque causes the threads 24 on the guard 20 loosen relative to the threads 26 on the body 12. In this way, the instrument remains easily accessible.

Because surgical instruments, including surgical knives, are typically handled with surgical gloves, guard 20 is preferably provided with a grip. The otherwise smooth outer surface of guard 20 may include a multitude of grips within the scope of the present invention. For example, as is shown in FIG. 3 and corresponding FIG. 3A (cross section of guard 20), a plurality of ridges 40 may be spaced around the outside circumference of guard 20. In FIG. 7 and corresponding FIG. 7A (cross section of guard 20) there is shown a plurality of bumps or nubs 42 dispersed around the outside circumference of guard 20. Any of the foregoing gripping means preferably form an exterior surface of the guard 20 which is not substantially smooth and cylindrical, and thus forming a surgical instrument that is easier to manipulate and not prone to inadvertently rolling off a sterile surgical field.

As would be understood by those skilled in the art, many different ways exist for assembling guard 20 on body 10. For example, portion 18 may screw into (or otherwise be fixedly attached to) handle portion 12 at or near threads 26, thus allowing guard 20 to be positioned on portion 18 prior to attachment to handle portion 12. Alternatively, guard 20 may be placed on portion 18 prior to attachment of tip 14. In any event, to prevent loss of guard 20, the particular means chosen for securing guard 20 onto the body 10 should preferably prevent inadvertent removal of guard 20 from body 10 during normal handling. Accordingly, during normal operation, guard 20 stays on the body 10 and forms an integral extension of the handle portion 12 during use of the instrument.

Although the foregoing figures and corresponding discussion illustrate threads as a preferred locking means, other locking means may be employed. For example, as would be understood by those skilled in the art, the locking means may include two or more grooves formed on the interior of guard 20 series that lock guard 20 open or closed by interaction with matching spring-loaded balls. In a similar manner, other types of spring-loaded (coiled spring or leaf spring) detents may be employed to "click" into grooves or notches in order to lock guard 20 into one of its two positions. Other examples not shown would include a bowed leaf spring attached at both ends of a reduced diameter portion, with a rounded projection on their upper-most portion to serve as a spring-loaded detent. In addition, a snap ring arrangement could be used as a detent to "click" into grooves to lock guard 20 into position.

Although the foregoing embodiments of the present invention and their corresponding advantages have been described in detail, it should be understood that various changes, substitutions, and alterations can be made herein without departing from the spirit and scope of the invention as defined by the appended claims.

What is claimed is:

1. A surgical device comprising:
   a body having a handle portion and a distal end with an instrument extending therefrom; and
   a guard member disposed around the body being selectively slidable along and around the body, the guard member comprising:
   a first opening formed for receiving a reduced diameter portion of the body;
   a second opening formed opposite the first opening for receiving the distal end of the body;
   a third opening formed between the first and second openings and extending to the first opening partially exposing the body; and
   a means for locking the guard member in either an open position to expose the instrument, or a closed position to protect the instrument comprising threads.

2. The surgical device of claim 1 further comprising a grip on the guard member.

3. The surgical device of claim 2 wherein the guard member is translucent.

4. The surgical device of claim 1 wherein the guard member is translucent.

5. The surgical device of claim 1 wherein the guard member is translucent and includes a plurality of protrusions formed on the exterior the thereof.

6. The surgical device of claim 1 further including a plurality of protrusions formed on the exterior of the guard member, the protrusions facilitating movement of the guard member and reducing rolling capacity of the surgical device.

7. The surgical device of claim 6 wherein the threads include a first set of external threads and a second set of external threads on the reduced diameter portion of the body.

8. The surgical device of claim 1 wherein the threads include a first set of external threads and a second set of external threads on the reduced diameter portion of the body.

* * * * *